(12) United States Patent
Kim et al.

(10) Patent No.: US 10,633,511 B2
(45) Date of Patent: Apr. 28, 2020

(54) PLASTICIZER COMPOSITION AND METHOD OF PREPARING THE SAME

(71) Applicant: LG CHEM, LTD., Seoul (KR)

(72) Inventors: Hyun Kyu Kim, Daejeon (KR); Mi Yeon Lee, Daejeon (KR); Yun Ki Cho, Daejeon (KR); Jeong Ju Moon, Daejeon (KR); Joo Ho Kim, Daejeon (KR); Seok Ho Jeong, Daejeon (KR)

(73) Assignee: LG CHEM LTD., Seoul (KR)

( * ) Notice: Subject to any disclaimer, the term of this patent is extended or adjusted under 35 U.S.C. 154(b) by 70 days.

(21) Appl. No.: 15/735,017

(22) PCT Filed: Apr. 17, 2017

(86) PCT No.: PCT/KR2017/004115
§ 371 (c)(1),
(2) Date: Dec. 8, 2017

(87) PCT Pub. No.: WO2017/183874
PCT Pub. Date: Oct. 26, 2017

(65) Prior Publication Data
US 2018/0163019 A1 Jun. 14, 2018

(30) Foreign Application Priority Data

Apr. 22, 2016 (KR) .................. 10-2016-0049080
Apr. 13, 2017 (KR) .................. 10-2017-0047830

(51) Int. Cl.
| | | |
|---|---|---|
| C08K 5/12 | (2006.01) | |
| C07C 67/02 | (2006.01) | |
| C07C 67/54 | (2006.01) | |
| C07C 69/80 | (2006.01) | |
| C08K 5/00 | (2006.01) | |
| C07C 67/303 | (2006.01) | |

(52) U.S. Cl.
CPC ............... *C08K 5/12* (2013.01); *C07C 67/02* (2013.01); *C07C 67/303* (2013.01); *C07C 67/54* (2013.01); *C07C 69/80* (2013.01); *C08K 5/00* (2013.01); C07C 2601/14 (2017.05); C08K 2201/014 (2013.01)

(58) Field of Classification Search
CPC ...... C08K 5/12; C08K 5/00; C08K 2201/014; C07C 67/02; C07C 67/303; C07C 67/54; C07C 69/80; C07C 2601/14
USPC ........................................................ 524/291
See application file for complete search history.

(56) References Cited

U.S. PATENT DOCUMENTS

| | | |
|---|---|---|
| 7,208,545 B1 | 4/2007 | Brunner et al. |
| 2016/0272780 A1 | 9/2016 | Kim et al. |
| 2016/0376219 A1 | 12/2016 | Kim et al. |
| 2017/0015810 A1 | 1/2017 | Miyazaki et al. |

FOREIGN PATENT DOCUMENTS

| | | |
|---|---|---|
| EP | 3103834 A | 12/2016 |
| EP | 3124540 A | 2/2017 |
| JP | 2015217608 A | 12/2015 |
| JP | 2015223700 A | 12/2015 |
| WO | 2013156930 A1 | 10/2013 |
| WO | 2015119442 A | 8/2015 |
| WO | 2015119443 A1 | 8/2015 |
| WO | 2015147300 A1 | 10/2015 |

*Primary Examiner* — Josephine L Chang
(74) *Attorney, Agent, or Firm* — Dentons US LLP

(57) ABSTRACT

Provided are a plasticizer composition, a method of preparing the same, and a resin composition including the same. The plasticizer composition is a mixed composition of cyclohexane 1,3-diester-based materials prepared by transesterification and hydrogenation, and when used in the resin composition, exhibits excellent resistance to stress, and excellent physical properties such as migration resistance and volatility resistance as well as tensile strength and an elongation rate.

11 Claims, No Drawings

PLASTICIZER COMPOSITION AND METHOD OF PREPARING THE SAME

CROSS-REFERENCE TO RELATED APPLICATION

This application is a National Stage Application of International Application No. PCT/KR2017/004115, filed Apr. 17, 2017, and claims the benefit of Korean Patent Application No. 10-2017-0047830, filed Apr. 13, 2017, Korean Patent Application No. 10-2016-0049080, filed Apr. 22, 2016, contents of which are incorporated herein by reference in their entirety for all purposes as if fully set forth below.

BACKGROUND

1. Field of the Invention

The present invention relates to a plasticizer composition, a method of preparing the same, and a resin composition comprising the same, and more particularly, to a plasticizer composition including hydrides of isophthalate-based materials with 3 types of compositions, a method of preparing the same and a resin composition comprising the same.

2. Discussion of Related Art

Conventionally, a plasticizer forms an ester through a reaction between an alcohol and a polycarboxylic acid such as phthalic acid and adipic acid. In addition, in consideration of domestic and international regulations for phthalate-based plasticizers harmful to humans, there is ongoing research on plasticizer compositions that can replace phthalate-based plasticizers, such as terephthalate-, adipate-, and other polymer-based plasticizers.

Meanwhile, there is an increasing demand for environmentally friendly products relating to flooring materials, wallpaper, soft and hard sheets, etc. obtained in the plastisol industry, the calendering industry, the extruding/injecting compound industry, etc., and in order to reinforce quality characteristics, processability and productivity of each end product for such environmentally friendly products, suitable plasticizers have to be used depending on discoloration, migration, mechanical properties, etc.

Depending on properties required by industry in various areas of use, such as tensile strength, an elongation rate, light fastness, a migration property, gelability or an absorption rate, a PVC resin is mixed with a supplementary material such as a plasticizer, a filler, a stabilizer, a viscosity depressant, a dispersant, an antifoaming agent or a foaming agent.

As an example, among plasticizer compositions applicable to PVC, when di(2-ethylhexyl)terephthalate which is relatively cheap and most widely used is applied, a plasticizer exhibits high hardness or sol viscosity, a relatively low absorption rate, and poor migration and stress migration. To improve these properties, it is expected that the quality of a plasticizer is enhanced through hydrogenation of terephthalate, but there is also a limitation in improving the quality by the basic structure of terephthalate.

Therefore, it is necessary to develop a new environmentally friendly plasticizer, which is eco-friendly or non-phthalate-based, and satisfies various properties such as volatile loss, migration loss, etc., as well as processability, hardness, tensile strength, and an elongation rate of a resin.

SUMMARY OF THE INVENTION

The present invention is directed to providing a cyclohexane 1,3-diester-based material that may be environmentally friendly and may have excellent physical properties as a new compound for a plasticizer, and as such a material is included in a plasticizer composition, the plasticizer composition can realize physical properties such as tensile strength, an elongation rate, etc. at the same or higher levels than a conventional plasticizer, as well as the reduction of migration loss and volatile loss.

In one aspect of the present invention, a plasticizer composition of the present invention comprises a hybrid-type cyclohexane 1,3-diester-based material represented by Formula 1.

[Formula 1]

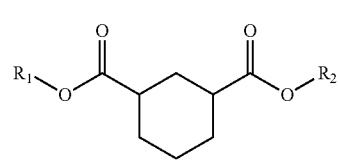

In Formula 1, $R_1$ and $R_2$ are different, and each independently a substituted or unsubstituted alkyl group having 3 to 10 carbon atoms; a substituted or unsubstituted alkylaryl group having 7 to 20 carbon atoms; a substituted or unsubstituted arylakyl group having 7 to 20 carbon atoms; or a substituted or unsubstituted aryl group having 6 to 20 carbon atoms.

In Formula 1, a substituent of the alkyl group may be an alkyl group having 1 to 6 carbon atoms; an alkenyl group having 2 to 6 carbon atoms; or an alkynyl group having 2 to 6 carbon atoms.

In Formula 1, $R_1$ and $R_2$ are different, and each independently a linear alkyl group having 3 to 10 carbon atoms; a branched alkyl group having 3 to 10 carbon atoms, which comprises one or more C1-C4 alkyl groups as a substituent; a phenyl group; or a benzyl group.

In Formula 1, $R_1$ and $R_2$ may be different, and each independently selected from the group consisting of a butyl group, an isobutyl group, a 2-ethylhexyl group, an isononyl group, a 2-propylheptyl group, an isodecyl group and a benzyl group.

In another aspect of the present invention, a method of preparing a plasticizer composition of the present invention comprises: providing an isophthalate-based material represented by Formula 4; and preparing a cyclohexane 1,3-diester-based material or a mixed composition thereof by hydrogenating one or more of the isophthalate-based materials in the presence of a metal catalyst.

[Formula 4]

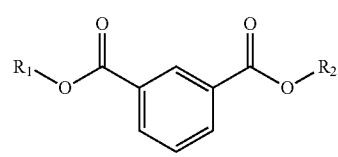

In still another aspect of the present invention, a resin composition of the present invention comprises 100 parts by weight of a resin; and 5 to 100 parts by weight of the above-described plasticizer composition.

The resin may comprise one or more selected from the group consisting of ethylene vinyl acetate, polyethylene, polypropylene, polyketone, polyvinyl chloride, polystyrene, polyurethane, a thermoplastic elastomer and poly(lactic acid).

DETAILED DESCRIPTION OF EXEMPLARY EMBODIMENTS

Hereinafter, to help in understanding the present invention, the present invention will be described in further detail.

It should be noted that terms and words used herein and in the claims should not be interpreted as being limited to a conventional or literal meaning, but should be interpreted with meanings and concepts which are consistent with the technological scope of the invention based on the principle that the inventors have appropriately defined concepts of terms in order to describe the invention in the best way.

Cyclohexane 1,3-diester-based Material

According to an exemplary embodiment of the present invention, a cyclohexane 1,3-diester-based material is represented by Formula 1 below, and is a hybrid type.

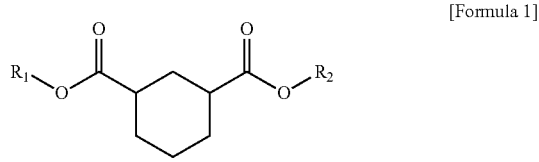

[Formula 1]

In Formula 1, $R_1$ and $R_2$ are different, and each independently a substituted or unsubstituted alkyl group having 3 to 10 carbon atoms; a substituted or unsubstituted alkylaryl group having 7 to 20 carbon atoms; a substituted or unsubstituted arylalkyl group having 7 to 20 carbon atoms; or a substituted or unsubstituted aryl group having 6 to 20 carbon atoms.

The hybrid type may mean that substituents linked to both ester groups, that is, $R_1$ and $R_2$, are different.

The cyclohexane 1,3-diester-based material may be used as a material comprised in a plasticizer, and when used as a plasticizer, include one or more substituents in the case that the $R_1$ and $R_2$ in Formula 1 are substituted alkyl groups, wherein the substituent may be an alkyl group having 1 to 6 carbon atoms; an alkenyl group having 2 to 6 carbon atoms; or an alkynyl group having 2 to 6 carbon atoms.

In addition, in Formula 1, $R_1$ and $R_2$ may be different, and each independently a linear alkyl group having 3 to 10 carbon atoms; a branched alkyl group having 3 to 10 carbon atoms, which comprises one or more C1-C4 alkyl groups as a substituent; a phenyl group; or a benzyl group.

In Formula 1, $R_1$ and $R_2$ may be preferably, for example, selected from the group consisting of a butyl group, an isobutyl group, a 2-ethylhexyl group, an isononyl group, a 2-propylheptyl group, an isodecyl group or a benzyl group, but the present invention is not limited thereto.

The cyclohexane 1,3-diester-based material may exhibit excellent physical properties when used as a plasticizer depending on which substituent is selected as each of $R_1$ and $R_2$ of Formula 1, and is preferably a linear alkyl group or branched alkyl group having 3 to 10 carbon atoms, or a phenyl group or benzyl group, and when the exemplified substituent is bound, it is more preferable for the present invention.

Specifically, the cyclohexane 1,3-diester-based material represented by Formula 1 may be composed of any of various compositions of $R_1$ and $R_2$. For example, the cyclohexane 1,3-diester-based material may be a compound in which $R_1$ and $R_2$ are respectively a 2-ethylhexyl group and a 2-propylheptyl group, $R_1$ and $R_2$ are respectively a 2-propylheptyl group and an isononyl group, $R_1$ and $R_2$ are respectively a 2-ethylhexyl group and an isononyl group, $R_1$ and $R_2$ are respectively an (iso)butyl group and a 2-ethylhexyl group, $R_1$ and $R_2$ are respectively an (iso)butyl group and an isononyl group, $R_1$ and $R_2$ are respectively an (iso)butyl group and an isodecyl group, $R_1$ and $R_2$ are respectively an (iso)butyl group and a benzyl group, $R_1$ and $R_2$ are respectively a 2-ethylhexyl group and an isodecyl group, $R_1$ and $R_2$ are respectively a 2-ethylhexyl group and a benzyl group, $R_1$ and $R_2$ are respectively a 2-propylheptyl group and an isodecyl group, $R_1$ and $R_2$ are respectively a 2-propylheptyl group and a benzyl group, $R_1$ and $R_2$ are respectively an isononyl group and an isodecyl group, $R_1$ and $R_2$ are respectively an isononyl group and a benzyl group, $R_1$ and $R_2$ are respectively an isodecyl group and a benzyl group, or $R_1$ and $R_2$ are respectively an (iso)butyl group and a 2-propylheptyl group.

The hybrid-type cyclohexane 1,3-diester-based material according to an exemplary embodiment of the present invention is a new compound used for a plasticizer, which has excellent purity and low contents of a residual alcohol and water, and when used in a resin composition, the material may be environmentally friendly, have a short absorption rate with respect to a resin and a short melting time to improve the processability of a resin, and provide excellent physical properties.

The hybrid-type cyclohexane 1,3-diester-based material may be a compound having an ester (—COO—) group at C1 and C3 positions of a cyclohexane ring, which may be derived from isophthalate according to a representative method. The hybrid-type cyclohexane 1,3-diester-based material may be environmentally friendly, and exhibit excellent physical properties such as migration resistance, volatility resistance, etc. as well as tensile strength and an elongation rate, compared to a compound having ester groups at C1 and C2 positions derived from a phthalate or compounds for a plasticizer based on a benzene ring.

Particularly, to prepare a phthalate-based ester compound having an ester group at an ortho-position, a benzenedicarboxylic acid used as a raw material has limitations of not being free from the problem of environmental pollution and the problem of harmfulness to the human body, and an isophthalate-based ester compound having an ester group at a para-position or a cyclohexane-1,4-dicarboxylate-based compound derived therefrom may be relatively decreased in compatibility with a resin and binding stability due to a linear structure, and act as a factor adversely affecting processability and workability of a product.

However, when used as a plasticizer of the resin composition, the hybrid-type cyclohexane 1,3-diester-based material may ensure the same levels of tensile strength and elongation rate, compared to a phthalate-based compound generally used as a conventional plasticizer, and reduce a migration loss (%) and a volatile loss (%), which particularly indicate a reduced amount of the plasticizer (a degree of detaching the plasticizer) present in a specimen, at considerable levels. That is, all physical properties may be realized at the same as or higher levels than those of the conventional plasticizer.

Plasticizer Composition

According to an exemplary embodiment of the present invention, a plasticizer composition comprises a hybrid-type cyclohexane 1,3-diester-based material represented by Formula 1 below.

[Formula 1]

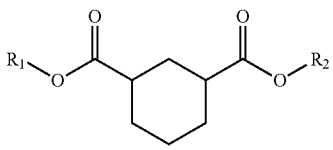

In Formula 1, $R_1$ and $R_2$ are different, and each independently a substituted or unsubstituted alkyl group having 3 to 10 carbon atoms; a substituted or unsubstituted alkylaryl group having 7 to 20 carbon atoms; a substituted or unsubstituted arylalkyl group having 7 to 20 carbon atoms; or a substituted or unsubstituted aryl group having 6 to 20 carbon atoms.

Descriptions of $R_1$ and $R_2$ are same each other as the descriptions on the cyclohexane 1,3-diester-based material, and therefore will be omitted.

In addition, the plasticizer composition may comprise two or more of the hybrid-type cyclohexane 1,3-diester-based materials. That is, while the above-described cyclohexane 1,3-diester-based materials may be independently used as a plasticizer, two or more of them may be mixed to realize a plasticizer composition. When the plasticizer composition is realized by mixing two or more cyclohexane 1,3-diester-based materials, various combinations of substituents may be applied, and examples for such substituent combinations are as described above.

The plasticizer composition may further comprise a non-hybrid-type cyclohexane 1,3-diester-based material represented by Formula 2, and a non-hybrid-type cyclohexane 1,3-diester-based material represented by Formula 3, and the non-hybrid type may mean that substituents binding to ester groups at both sides are same each other, unlike Formula 1.

[Formula 2]

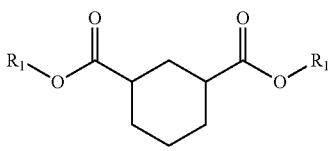

In Formula 2, $R_1$ is a substituted or unsubstituted alkyl group having 3 to 10 carbon atoms; a substituted or unsubstituted alkylaryl group having 7 to 20 carbon atoms; a substituted or unsubstituted arylalkyl group having 7 to 20 carbon atoms; or a substituted or unsubstituted aryl group having 6 to 20 carbon atoms.

[Formula 3]

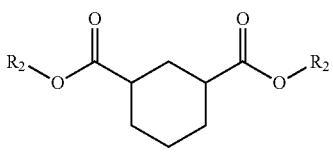

In Formula 3, $R_2$ is a substituted or unsubstituted alkyl group having 3 to 10 carbon atoms; a substituted or unsubstituted alkylaryl group having 7 to 20 carbon atoms; a substituted or unsubstituted arylalkyl group having 7 to 20 carbon atoms; or a substituted or unsubstituted aryl group having 6 to 20 carbon atoms.

In Formulas 2 and 3, $R_1$ and $R_2$ may be selected from the same ranges of $R_1$ and $R_2$ of Formula 1 as described above.

In addition, when the plasticizer composition comprises three types of compounds such as the cyclohexane 1,3-diester-based materials represented by Formulas 1 to 3, each of $R_1$ and $R_2$ may be the same in Formulas 1 to 3. Specifically, $R_1$ of Formula 1 may be the same as $R_1$ of Formula 2, and $R_2$ of Formula 1 may be the same as $R_2$ of Formula 3.

Here, the cyclohexane 1,3-diester-based materials represented by Formulas 1 to 3 may be specifically made in the following combinations, but the combinations of the compounds for realizing the plasticizer composition are not limited to the following examples.

The plasticizer composition may be a composition composed of three types of the cyclohexane 1,3-diester-based materials in which carboxylate groups are bound at C1 and C3 of the cyclohexane, and may be a composition formed when an isophthalate-based material is di(2-ethylhexyl) isophthalate in the preparation method described above.

Specifically, in the plasticizer composition, the compound of Formula 1 may be butyl (2-ethylhexyl) cyclohexane-1,3-dicarboxylate (1,3-BOCH), the compound of Formula 2 may be dibutyl cyclohexane-1,3-dicarboxylate (1,3-DBCH), and the compound of Formula 3 may be bis(2-ethylhexyl) cyclohexane-1,3-dicarboxylate (1,3-DOCH).

In addition, in the plasticizer composition, the compound of Formula 1 may be isobutyl (2-ethylhexyl) cyclohexane-1,3-dicarboxylate (1,3-iBOCH), the compound of Formula 2 may be diisobutyl cyclohexane-1,3-dicarboxylate (1,3-DiBCH), and the compound of Formula 3 may be bis(2-ethylhexyl) cyclohexane-1,3-dicarboxylate (1,3-DOCH).

In addition, in the plasticizer composition, the compound of Formula 1 may be isononyl (2-ethylhexyl) cyclohexane-1,3-dicarboxylate (1,3-OINCH), the compound of Formula 2 may be diisononyl cyclohexane-1,3-dicarboxylate (1,3-DINCH), and the compound of Formula 3 may be bis(2-ethylhexyl) cyclohexane-1,3-dicarboxylate (1,3-DOCH).

Meanwhile, the cyclohexane 1,3-diester-based materials represented by Formulas 1 to 3 may be included at composition ratios as follows.

The plasticizer composition may comprise 0.5 to 70 wt % of the cyclohexane dicarboxylate represented by Formula 1; 0.5 to 50 wt % of the cyclohexane dicarboxylate represented by Formula 2; and 0.5 to 85 wt % of the cyclohexane dicarboxylate represented by Formula 3 based on the total weight of the plasticizer composition.

Preferably, the plasticizer composition may comprise 10 to 50 wt % of the cyclohexane dicarboxylate represented by Formula 1; 0.5 to 50 wt % of the cyclohexane dicarboxylate represented by Formula 2; and 35 to 80 wt % of the cyclohexane dicarboxylate represented by Formula 3 based on the total weight of the plasticizer composition.

As the plasticizer composition comprises the cyclohexane 1,3-diester-based materials of Formulas 1 to 3 at the above-described specific range of weight ratios, the plasticizer composition may further improve processability of a resin due to an absorption rate with respect to a resin and a short melting time, and further improve physical properties such as hardness, tensile strength, an elongation rate, a migration loss, a sheet volatile loss, heat stability and an accelerated weathering resistance (QUV).

In the plasticizer composition, the sum of a non-hybrid-type cyclohexane 1,3-diester-based material represented by Formula 2 and a non-hybrid-type cyclohexane 1,3-diester-based material represented by Formula 3, and a hybrid-type cyclohexane dicarboxylate represented by Formula 1 may be included at a weight ratio of 95:5 to 30:70.

That is, it can be understood that the weight ratio of the non-hybrid type to the hybrid-type is 95:5 to 30:70.

When used as a plasticizer of the resin composition, the plasticizer composition may ensure equal levels of hardness, tensile strength and an elongation rate, compared to a phthalate-based compound conventionally used as a conventional plasticizer, reduce a volatile loss, and have considerably excellent migration resistance and excellent resistance to stress.

Method of Preparing Plasticizer Composition

According to an exemplary embodiment of the present invention, a method of preparing a plasticizer composition comprises: providing an isophthalate-based material represented by Formula 1 below; and preparing a cyclohexane 1,3-diester-based material or a mixed composition thereof by hydrogenating one or more of the isophthalate-based materials in the presence of a metal catalyst.

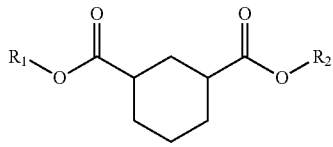

[Formula 1]

In Formula 1, $R_1$ and $R_2$ are different, and each independently a substituted or unsubstituted alkyl group having 3 to 10 carbon atoms; a substituted or unsubstituted alkylaryl group having 7 to 20 carbon atoms; a substituted or unsubstituted arylalkyl group having 7 to 20 carbon atoms; or a substituted or unsubstituted aryl group having 6 to 20 carbon atoms.

Descriptions of the substituents $R_1$ and $R_2$ are same each other as described in Formulas 1 to 3.

The method of preparing a plasticizer composition may be a method of preparing a cyclohexane 1,3-diester-based material when one type of isophthalate-based material is applied in the preparation of an isophthalate-based material.

The provision of an isophthalate-based material may be preparation of an isophthalate-based material, for example, using transesterification or direct esterification. To prepare an isophthalate-based material having $R_1$ and $R_2$, which are different, both of the transesterification and the direct esterification may be used, and to prepare an isophthalate-based material having $R_1$ and $R_2$, which are same each other, and only one type of isophthalate-based material, direct esterification may be used.

The provision of an isophthalate-based material may comprise conducting transesterification of an isophthalate-based material and an alcohol, in which the alcohol may be an alkyl alcohol having a substituted or unsubstituted alkyl group having 3 to 10 carbon atoms, and in consideration of the above-described substituent combination, an alcohol may be suitably selected.

When the transesterification is used, a plasticizer composition in which three types of cyclohexane 1,3-diester-based materials are mixed may be prepared, and in this case, the plasticizer composition having a specific combination and a specific composition ratio may be prepared.

The term "transesterification" used herein refers to a reaction between an alcohol and an ester by Reaction Scheme 1 below, and particularly, to an interchange between "R'''" of the ester and "R'" of the alcohol as shown in Reaction Scheme 1 below:

[Reaction Scheme 1]

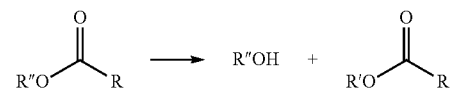

When the transesterification is conducted, a product may be composed of a compound (hereinafter, referred to as a "dual attack ester compound") formed by the attack of the carbon of a carbonyl group in two ester groups (RCOOR") present in the dioctylisophthalate by an alkoxide group of the alcohol; a compound (hereinafter, referred to as a "single attack ester compound") formed by the attack of the carbon of one ester group (RCOOR"); and a compound (hereinafter, referred to as a "reaction residual ester compound") remaining as an non-reactant that does not participate in a reaction.

The transesterification may be a non-catalytic reaction, and therefore may not cause a waste water problem, compared to acid-alcohol esterification, and may solve problems caused by the use of an acidic catalyst.

As three types of compounds produced by the transesterification, a single-attack ester compound (when an alcohol reacts with one of two ester groups), a dual-attack ester compound (when an alcohol reacts with all of two ester groups), and a reaction residual ester compound (not reacted) may be formed at 0.5 to 70 wt %, 0.5 to 50 wt %, and 0.5 to 85 wt %, respectively, and specifically, 10 to 50 wt %, 0.5 to 50 wt %, and 35 to 80 wt % based on the total weight of an ester-based composition.

In this case, when all or none of the two ester groups are reacted, the compound may be a non-hybrid type, and when only one ester group is reacted, the compound may be a hybrid type, and in this case, the weight ratio of the non-hybrid type and the hybrid-type may be 95:5 to 30:70.

That is, the cyclohexane dicarboxylate represented by Formula 2 and the cyclohexane dicarboxylate represented by Formula 3 may be derived from a dual-attack ester-based compound and a reaction residual ester-based compound in transesterification. Since substituents binding to a dicarboxylate group of the cyclohexane are the same, the compound may be a non-hybrid type, and since the cyclohexane dicarboxylate represented by Formula 1 is derived from a single attack ester-based compound and has two different substituents, the compound may be a hybrid type.

When a plasticizer composition comprising two or more (specifically, three types) of the cyclohexane 1,3-diester-based materials from the isophthalate-based materials obtained in the above range is prepared, the plasticizer composition may have high process efficiency and excellent processability and an excellent absorption rate.

The ester-based composition prepared in the transesterification may comprise all of a single-attack ester compound, a dual-attack ester compound and a reaction residual ester compound, and a composition ratio of the ester-based composition may be controlled according to an amount of the alcohol added.

The amount of the alcohol added may be 0.1 to 89.9 parts by weight, specifically, 3 to 50 parts by weight, and more specifically, 5 to 40 parts by weight based on 100 parts by weight of the isophthalate-based material.

The ester-based composition may have an increased mole fraction of an isophthalate-based material participating in the transesterification with the increased amount of alcohol added, and therefore, in the plasticizer composition, contents of the single-attack ester compound and the dual-attack ester compound may be increased.

Accordingly, it also can be shown that a content of the unreacted reaction residual ester compound present tends to be reduced.

A molar ratio of the isophthalate-based material and the alcohol may be, for example, 1:0.005 to 5.0, 1:0.05 to 2.5, or 1:0.1 to 1.0, and in this range, the ester-based composition may provide a plasticizer composition having high process efficiency and an excellent effect of improving processability.

The transesterification may be conducted at 120 to 190° C., preferably 135 to 180° C., and more preferably 141 to 179° C. for 10 minutes to 10 hours, preferably 30 minutes to 8 hours, and more preferably 1 to 6 hours, and thus an ester-based composition having a desired composition ratio may be effectively obtained within the above-described temperature and time ranges. Here, the reaction time may be calculated from the point of time to reach a reaction temperature after reactants are heated.

The transesterification may be a non-catalytic reaction, but in some cases, may be performed under an acidic catalyst or metal catalyst, which reduces a reaction time.

The acidic catalyst may be, for example, sulfuric acid, methanesulfonic acid or p-toluenesulfonic acid, and the metal catalyst may be, for example, an organic metal catalyst, a metal oxide catalyst, a metal salt catalyst or a metal itself.

The metal component may be, for example, any one selected from the group consisting of tin, titanium and zirconium, or a mixture of two or more thereof.

When the transesterification is used, an ether-free composition which is a product without ether may be prepared, and therefore, a waste water problem or a problem in which a process uses a special separation process may be solved.

After the transesterification, removal of a unreacted alcohol and a reaction byproduct such as an isophthalate-based material through distillation may be further included.

The distillation may be, for example, two-step distillation for separating each of the alcohol and the reaction byproduct according to a difference in boiling points, or as another example, the distillation may be mixed distillation. In this case, a desired composition ratio of the ester-based composition may be relatively and stably ensured. The mixed distillation refers to simultaneous distillation of both of butanol and a reaction byproduct.

Types and contents of mixed components of a produced isophthalate-based material may depend on combination and reaction ratios of the isophthalate-based material and an alcohol used in the transesterification, and thereby the combination of specific compounds of the plasticizer composition comprising a cyclohexane 1,3-diester-based material which is finally produced may be changed.

In addition, the provision of an isophthalate-based material may comprise preparing an isophthalate-based material by direct esterification between isophthalic acid and an alcohol in the presence of a catalyst.

The alcohol used in the direct esterification may be an alkyl alcohol having a substituted or unsubstituted alkyl group having 3 to 10 carbon atoms, and may be suitably selected according to which substituent is included in the isophthalate-based material to be prepared. In Formula 4, when $R_1$ and $R_2$ are same each other, only one type of alcohol may be subjected to the reaction, when $R_1$ and $R_2$ are different, two types of alcohols may participate in the reaction, and when several types of isophthalate-based materials will be prepared at once, three or more types of alcohols may participate in the reaction. However, when too many types of alcohols participate in the reaction, it may be difficult to control the reaction and detect which isophthalate is included in the prepared product, and therefore suitable selection may be required.

In the direct esterification, the dicarboxylic acid-based compound comprises isophthalate, and the alcohol may comprise 2-ethylhexyl alcohol.

The direct esterification may be performed in a temperature range of 80 to 270° C. and preferably 150 to 250° C. for 10 minutes to 10 hours, preferably 30 minutes to 8 hours, and more preferably 1 to 6 hours. Within the above temperature and time ranges, the isophthalate-based material may be effectively obtained.

A catalyst for the direct esterification may be a Sn- or Ti-based organic metal catalyst, a sulfate- or sulfonate-based acidic catalyst, or a mixed catalyst thereof, and is not limited to a catalyst type.

The dicarboxylic acid-based compound and the alcohol may be used at a molar ratio of 1:1 to 7, and preferably 1:2 to 5.

The alcohol may be prepared by a conventional method, or commercially available. The commercially available alcohol may be mixed with one type or more of alcohol isomers, and the alcohol and an isomer thereof may be included at a ratio of, for example, 50 to 100 parts by weight: 0 to 50 parts by weight, and preferably, 70 to 100 parts by weight: 0 to 30 parts by weight.

The alcohol comprising an isomer may be prepared in the form of a mixture in which an isophthalate-based material and an isomer thereof are mixed. In addition, therefore, in the ester-based composition according to an exemplary embodiment of the present invention, each compound may further comprise many isomers.

The isophthalate-based material may be prepared at a yield of approximately 80% or more by the direct esterification for preparing the isophthalate-based material, and a desired composition may be easily prepared by the transesterification between the isophthalate-based material prepared as described above and the alcohol.

A method of preparing the plasticizer composition may comprise preparing a cyclohexane 1,3-diester-based material or a mixed composition thereof by hydrogenation of one or more of the isophthalate-based materials in the presence of a metal catalyst.

The hydrogenation may be a process for converting an isophthalate-based material into a cyclohexane 1,3-diester-based material by hydrogenation of single compounds or a mixture thereof such as the isophthalate-based material in the presence of a metal catalyst.

The hydrogenation may be a reaction for removing the aromaticity of benzene rings of the isophthalate-based materials by adding hydrogen in the presence of a metal catalyst, which may be a type of reduction.

The hydrogenation is for synthesizing a cyclohexane 1,3-diester-based material by reacting the isophthalate-based material with hydrogen in the presence of a metal catalyst, and conditions for the reaction may comprise all conventional reaction conditions for hydrogenating only benzene rings without affecting carbonyl groups substituted in the benzene.

The hydrogenation may be performed with an additional organic solvent such as ethanol, but the present invention is not limited thereto. As a metal catalyst, generally, an Rh/C catalyst, a Pt catalyst or a Pd catalyst, which is used for hydrogenation of a benzene ring, may be used, but any catalyst that can be used in such hydrogenation may be used without limitation.

For example, in the hydrogenation, a pressure for the hydrogen addition may be approximately 3 to 15 MPa, and the reaction may be performed for approximately 2 to 10 hours and at a temperature of approximately 80 to 200° C.

The above-described reaction may be an example, and a final hydrogenated cyclohexane 1,3-diester-based material may be prepared by first preparing a hydrogenated cyclohexane 1,3-diester-based material of a single material by hydrogenating isophthalate of the single material, and preparing a mixed cyclohexane 1,3-diester-based composition, which is hydrogenated by transesterification using an alcohol.

In other words, a final product may be prepared by hydrogenating isophthalic acid and/or isophthalate through direct esterification and/or transesterification, and any method of preparing a hydrogenated mixture through transesterification after hydrogenation of isophthalate prepared by esterification may be applied.

Meanwhile, the final mixed composition comprising three types of the final hydrogenated materials, which is prepared by transesterification, may generally comprise two types of materials having the same alkyl groups of a diester and one type of material having different alkyl groups of a diester. Here, the one type of material having different alkyl groups of the diester may act as a main factor affecting the physical properties of a plasticizer, but it may be commercially and technically impossible to be separated into single materials.

For example, while a material having the same alkyl groups binding to the diesters at the 1- and 3-positions can be prepared as a single material through direct esterification, a material having different alkyl groups binding to the diesters at the 1- and 3-positions of a cyclohexane may be prepared only by transesterification. In this case, it is impossible to separate only the material having different alkyl groups of the diester, and even if possible, the material can be separated in only a very small amount through excessive repetition at the laboratory level.

As an alternative, a method of realizing a composition having optimal physical properties by controlling the number of carbon atoms in an alkyl group or a ratio of three compositions in the final composition state may be applied.

When a cyclohexane 1,3-diester-based material or a mixed composition thereof is prepared using an isophthalate-based material through such hydrogenation, component ratios may be maintained almost at the same levels.

Resin Composition

According to another exemplary embodiment of the present invention, a resin composition comprising the above-described plasticizer composition and a resin is provided.

The resin may be any resin known in the art. For example, the resin may be a mixture of one or more selected from ethylene vinyl acetate, polyethylene, polypropylene, polyvinyl chloride, polystyrene, polyurethane, a thermoplastic elastomer and poly(lactic acid), but the present invention is not limited thereto.

The plasticizer composition may be included at 5 to 150 parts by weight based on 100 parts by weight of the resin. In addition, the plasticizer composition is preferably included at 5 to 100 parts by weight, 10 to 100 parts by weight, or 30 to 100 parts by weight.

The resin composition may further comprise a filler. The filler may be included at 0 to 300 parts by weight, preferably 50 to 200 parts by weight, and more preferably 100 to 200 parts by weight based on 100 parts by weight of the resin.

The filler may be any filler known in the art, but the present invention is not particularly limited. For example, the filler may be a mixture of one or more selected from silica, magnesium carbonate, calcium carbonate, hard charcoal, talc, magnesium hydroxide, titanium dioxide, magnesium oxide, calcium hydroxide, aluminum hydroxide, aluminum silicate, magnesium silicate and barium sulfate.

In addition, the resin composition may further comprise other additives such as a stabilizer, etc., as needed. Each of the additives such as a stabilizer may be included at, for example, 0 to 20 parts by weight, and preferably 1 to 15 parts by weight based on 100 parts by weight of the resin.

The stabilizer may be, for example, a calcium-zinc-based (Ca—Zn-based) stabilizer such as a calcium-zinc composite stearate salt, but the present invention is not particularly limited thereto.

The resin composition may have viscosity of a sol of 4,000 to 15,000 cp, 5,000 to 11,000 cp, or 6,000 to 9,000 cp, and stable processability can be ensured in this range.

The viscosity of the sol is measured using a Brookfield (LV type) viscometer with spindle #4 at 6 rpm and 12 rpm. For example, as a sample, plastisol is prepared by mixing 100 phr of PVC (PB900, LG Chem), 75 phr of the plasticizer composition, 4 phr of a stabilizer (KSZ111XF), 3 phr of a foaming agent (W1039), 13 phr of $TiO_2$ (TMCA100), 130 phr of $CaCO_3$ (OMYA10), 10 phr of a viscosity depressant (Exa-sol) and 1 phr of a dispersant (BYK3160), and stored at 25° C. for 1 hour before the measurement of the viscosity of the sol.

For example, the resin composition may be a resin composition lowering an input of a viscosity depressant compared to a conventional product or not using a viscosity depressant, that is, a viscosity depressant-free resin composition.

The viscosity depressant-free composition does not comprise any viscosity depressant for controlling a viscosity of the resin composition.

The plasticizer composition of the present invention described above may have an absorption rate with respect to the resin and a short melting time, thereby improving processability of the resin, and provide excellent physical properties in sheet formulations for wires, interior materials for automobile, films, sheets, tubes, wallpaper, toys, flooring, etc., plastisol formulations, and compound formulations.

EXAMPLES

Hereinafter, to explain the present invention in detail, the present invention will be described in detail with reference to examples. However, examples according to the present invention may be modified in a variety of different forms, and the scope of the present invention should not be construed as being limited to the examples to be described below. The exemplary embodiments of the present invention are provided for those of ordinary skill in the art to more fully understand the present invention.

Example 1

498.0 g of purified isophthalic acid (PIA), 586 g of 2-ethyl hexanol (2-EH), 721 g of 2-propyl heptanol (2-PH) (BASF) (the molar ratio of PIA:2-EH:2-PH-1.0:1.5:1.5), and 1.54 g (0.31 parts by weight based on 100 parts by weight of PIA) of a titanium-based catalyst (TIPT, tetra isopropyl titanate) as a catalyst were input into a 3 L 4-neck reaction vessel equipped with a cooler, a water stripper, a condenser, a decanter, a reflux pump, a temperature controller, an agitator, etc., and gradually heated to approximately 170° C. Water started to be generated at approximately 170° C., and esterification was performed for approximately 4.5 hours with continuous addition of nitrogen gas at a reaction temperature of approximately 220° C. under atmospheric pressure, and terminated when an acid value reached 0.01.

After the reaction was completed, to remove unreacted raw materials, distillation extraction was performed under reduced pressure for 0.5 to 4 hours. To remove unreacted raw materials to a predetermined content level or less, steam extraction was performed using steam under reduced pressure for 0.5 to 3 hours, and following lowering a temperature of a reaction solution, neutralizing treatment was performed using an alkali solution. Additionally, washing may be carried out, and then the reaction solution was dehydrated to remove moisture. A filtering material was input into the dehydrated reaction solution, and after stirring for a predetermined time and filtering, an isophthalate-based composition (yield: 99.0%) comprising 49 wt % of 2-ethylhexyl 2-propylheptyl isophthalate (EHPIP), 17 wt % of di-(2-ethylhexyl) isophthalate (DEHIP) and 34 wt % of di-(2-propylheptyl) isophthalate (DPIP) was obtained.

Afterward, as raw materials, 1,000 g of the composition produced by esterification and 20 g of a ruthenium catalyst (N.E CHEMCAT) were added into a 1.5 L high-pressure reaction vessel, hydrogenation were performed by adding hydrogen under a pressure of 8 MPa for 3 hours at 150° C., and then the reaction was terminated. After the reaction, the catalyst was filtered, a hydrogenated mixed composition was prepared through a conventional purification process at a yield of 99%.

Examples 2 to 7

A cyclohexane 1,3-dicarboxylate composition was obtained by the same method as described in Example 1, except that a combination of alcohols as shown in Table 1 below was used instead of 2-ethyl hexanol and 2-propyl heptanol.

TABLE 1

| | Cyclohexane 1,3-diester-based composition | | |
|---|---|---|---|
| Classification | Substituent of Formula 1 | Substituent of Formula 2 | Substituent of Formula 3 |
| Example 1 | 2-ethylhexyl/2-propylheptyl | di(2-ethylhexyl) | di(2-propylheptyl) |
| Example 2 | 2-propylheptyl/isononyl | di(2-propylheptyl) | diisononyl |
| Example 3 | 2-ethylhexyl/isononyl | di(2-ethylhexyl) | diisononyl |
| Example 4 | butyl/2-ethylhexyl | dibutyl | di(2-ethylhexyl) |
| Example 5 | butyl/2-propylheptyl | dibutyl | di(2-propylheptyl) |
| Example 6 | butyl/isononyl | dibutyl | diisononyl |
| Example 7 | isobutyl/2-ethylhexyl | diisobutyl | diisodecyl |

Comparative Example 1

As a widely-used environmentally friendly plasticizer, GL300 (LG Chem, DOTP) was used.

Comparative Example 2

Di(2-ethylhexyl) cyclohexane 1,3-dicarboxylate was obtained by performing the same method as described in Example 1, except that 2-ethyl hexanol was used as a single alcohol instead of 2-ethyl hexanol and 2-propyl heptanol.

Comparative Example 3

Di(2-ethylhexyl) cyclohexane 1,4-dicarboxylate was obtained by performing the same method as described in Comparative Example 1, except that terephthalic acid was used instead of isophthalic acid.

Comparative Example 4

A cyclohexane 1,4-dicarboxylate composition was obtained by performing the same method as described in Example 2, except that terephthalic acid was used instead of isophthalic acid.

Comparative Example 5

An isophthalate composition was obtained by performing the same method as described in Example 3, except that hydrogenation was not performed.

Summarizing Comparative Examples 1 to 5, results are shown in Table 2 below.

TABLE 2

| Classification | Material |
|---|---|
| Comparative Example 1 | di(2-ethylhexyl)terephthalate |
| Comparative Example 2 | di(2-ethylhexyl) cyclohexane-1,3-diester |
| Comparative Example 3 | di(2-ethylhexyl) cyclohexane-1,4-diester |
| Comparative Example 4 | mixed cyclohexane-1,4-diester composition of 2-propylheptyl/isononyl, di(2-propylheptyl) and diisononyl |
| Comparative Example 5 | isophthalate composition of 2-ethylhexyl/isononyl, di(2-ethylhexyl) and diisononyl |

Experimental Example 1: Evaluation of Physical Properties

Specimens for experiments were prepared using the plasticizer compositions of the Examples and Comparative Examples described in Tables 1 and 2.

The specimens were prepared, according to ASTM D638, by mixing 40 parts by weight of each of the plasticizer compositions of Examples 1 to 10 and Comparative Examples 1 to 5, 3 parts by weight of a stabilizer (BZ-153T) with 100 parts by weight of PVC (LS100S) with a 3 L super mixer at 98° C. and 700 rpm according to ASTM D638, performing roll milling at 160° C. for 4 minutes to form a 5 mm sheet, and performing pressing at 180° C. for 2.5 minutes under low pressure and for 2 minutes under high pressure to form 1T and 3T sheets. Physical properties of each specimen were evaluated by test items listed below, and the results are summarized in Table 3 below.

<Test Items for Physical Properties>

Measurement of Hardness

Shore hardness (SHORE A) was measured at 25° C. according to ASTM D2240.

Measurement of Tensile Strength

According to ASTM D638, each specimen was pulled at a cross head speed of 200 mm/min using a tensile testing instrument (U.T.M, Manufacturer; Instron, Model No.: 4466) and a position at which the specimen was broken was detected. A tensile strength was calculated as follows:

Tensile strength (kgf/mm$^2$)=Load value (kgf)/Thickness (mm)×Width(mm)

Measurement of Elongation Rate

According to ASTM D638, each specimen was pulled at a cross head speed of 200 mm/min using the U.T.M, and a position at which the specimen was broken was detected. An elongation rate was calculated as follows:

Elongation rate(%)=Length after elongation/Initial length×100.

Measurement of Migration Loss

An experimental specimen having a thickness of 2 mm or more was obtained according to KSM-3156, and after ABS (Natural Color) was attached to both sides of the specimen, a weight of 1 kgf/cm$^2$ was applied to the specimen. The specimen was put in a forced convection type oven (80° C.) for 72 hours, and cooled at room temperature for 4 hours. Then, after ABS that had been attached to both sides of the specimen was removed, a weight was measured before and after the specimen was put into the oven and thus a migration loss was calculated by the equation as follows:

Migration loss(%)=[(Initial weight of specimen at room temperature−Weight of specimen after being put into oven)/Initial weight of specimen at room temperature]×100

Measurement of Volatile Loss

The prepared specimen was processed at 100° C. for 72 hours, and a weight of the specimen was measured.

Volatile loss (wt %)=[(Weight of initial specimen−Weight of specimen after processed at 100° C. for 72 hours)/Weight of initial specimen]×100

Stress Test

A stress test was performed by leaving the specimens at room temperature for 24, 72 and 168 hours, respectively, while bent, to observe a migration degree (a leaking degree), which was expressed as a numerical value. A value closer to 0 indicates a superior property.

QUV Test

According to ASTM 4329-13, UV radiation was performed at a QUV internal temperature of 60° C. for 200 hours, E for each specimen was confirmed using a spectrophotometer.

TABLE 3

| Classification | Hardness (Shore "A") | Tensile strength (kg/cm$^2$) | Elongation rate (%) | Migration loss (%) | Volatile loss (%) | QUV (ΔE) | Stress test |
|---|---|---|---|---|---|---|---|
| Example 1 | 88.5 | 305.8 | 320.6 | 1.20 | 1.05 | 0.87 | 0.5 |
| Example 2 | 89.0 | 310.5 | 338.1 | 1.01 | 0.78 | 1.00 | 0.5 |
| Example 3 | 88.0 | 299.0 | 327.9 | 1.10 | 1.20 | 1.18 | 0.5 |
| Example 4 | 86.5 | 288.3 | 330.2 | 1.68 | 2.33 | 1.03 | 0 |
| Example 5 | 87.0 | 290.5 | 325.0 | 1.74 | 1.85 | 0.68 | 0 |
| Example 6 | 88.0 | 296.0 | 322.7 | 1.78 | 1.50 | 0.80 | 0.5 |
| Example 7 | 86.5 | 271.8 | 322.0 | 1.80 | 2.40 | 0.88 | 0 |
| Comparative Example 1 | 93.0 | 253.6 | 312.0 | 3.56 | 0.88 | 3.77 | 3.0 |
| Comparative Example 2 | 89.0 | 270.2 | 308.5 | 2.89 | 2.10 | 1.10 | 1.0 |
| Comparative Example 3 | 88.0 | 275.0 | 298.7 | 3.80 | 2.00 | 1.22 | 2.0 |
| Comparative Example 4 | 92.5 | 256.3 | 265.1 | 4.22 | 1.80 | 1.18 | 2.0 |
| Comparative Example 5 | 90.5 | 265.5 | 287.0 | 3.40 | 2.33 | 2.50 | 2.0 |

Referring to Table 3, when the plasticizer compositions of Examples 1 to 7 were applied, compared to the plasticizer compositions of Comparative Examples 1 to 5, it can be seen that plasticization efficiency was improved due to the overall low hardness, and it was confirmed that mechanical physical properties such as an elongation rate and a tensile strength were considerably improved. In addition, overall improvement in migration loss was made, and compared to the QUV results of Comparative Examples 1 and 5, which had not be hydrogenated, it can be seen that the hydrogenated products have excellent resistance to UV.

It can also be confirmed that the hydrogenated products exhibit excellent physical properties which also satisfy resistance to stress.

To this end, when a hybrid-type cyclohexane 1,3-diester-based material which have two different alkyl groups binding to the diester is used as a plasticizer, it can be seen that various physical properties are improved.

A plasticizer composition according to an exemplary embodiment of the present invention, when used in a resin composition, can provide excellent physical properties such as migration resistance and volatility resistance, etc. as well as tensile strength and an elongation rate, and provide a resin product having excellent resistance to stress, and also provide a plasticizer composition including cyclohexane 1,3-diester-based materials through hydrogenation by preparing one or two or more isophthalate-based materials having specific component ratios using direct esterification or transesterification.

While the present invention has been described in detail with reference to exemplary embodiments of the present invention, it should be understood to those of ordinary skill in the art that the scope of the present invention is not limited thereto, but also includes various forms of modification and alternation based on the fundamental ideas of the present invention defined by the accompanying claims.

What is claimed is:

1. A plasticizer composition comprising hybrid-type and non-hybrid type cyclohexane 1,3-diester-based materials represented by Formulas 1-3:

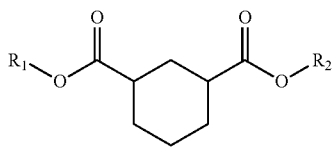
[Formula 1]

in Formula 1, $R_1$ and $R_2$ are different, and each independently a substituted or unsubstituted alkyl group having 3 to 10 carbon atoms; a substituted or unsubstituted alkylaryl group having 7 to 20 carbon atoms; a substituted or unsubstituted arylalkyl group having 7 to 20 carbon atoms; or a substituted or unsubstituted aryl group having 6 to 20 carbon atoms;

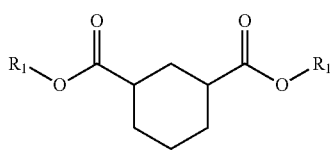
[Formula 2]

in Formula 2, $R_1$ is a substituted or unsubstituted alkyl group having 3 to 10 carbon atoms; a substituted or unsubstituted alkylaryl group having 7 to 20 carbon atoms; a substituted or unsubstituted arylalkyl group having 7 to 20 carbon atoms; or a substituted or unsubstituted aryl group having 6 to 20 carbon atoms; and

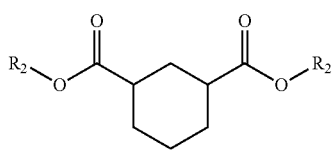
[Formula 3]

in Formula 3, $R_2$ is a substituted or unsubstituted alkyl group having 3 to 10 carbon atoms; a substituted or unsubstituted alkylaryl group having 7 to 20 carbon atoms; a substituted or unsubstituted arylalkyl group having 7 to 20 carbon atoms; or a substituted or unsubstituted aryl group having 6 to 20 carbon atoms.

2. The plasticizer composition of claim 1, wherein, in Formula 1, a substituent of the alkyl group is an alkyl group having 1 to 6 carbon atoms; an alkenyl group having 2 to 6 carbon atoms; or an alkynyl group having 2 to 6 carbon atoms.

3. The plasticizer composition of claim 1, wherein, in Formula 1, $R_1$ and $R_2$ are different, and each is a linear alkyl group having 3 to 10 carbon atoms; or a branched alkyl group having 3 to 10 carbon atoms, which comprises one or more alkyl groups having 1 to 4 carbon atoms as a substituent.

4. The plasticizer composition of claim 1, wherein, in Formula 1, $R_1$ and $R_2$ are different, and each independently selected from the group consisting of a butyl group, an isobutyl group, a 2-ethylhexyl group, an isononyl group, a 2-propylheptyl group and an isodecyl group.

5. The plasticizer composition of claim 1, wherein $R_1$ in Formulas 1 to 3 are each the same as one another, and $R_2$ in Formulas 1 to 3 are each the same as one another.

6. The plasticizer composition of claim 1, wherein a weight ratio of the sum of the non-hybrid-type cyclohexane 1,3-diester-based materials represented by C Formulas 2 and 3, to the hybrid-type cyclohexane 1,3-diester-based material of Formula 1 is 95:5 to 30:70.

7. The plasticizer composition of claim 1, which comprises:
based on the total weight of the plasticizer composition,
0.5 to 70 wt % of a hybrid-type cyclohexane 1,3-diester-based material represented by Formula 1;
0.5 to 50 wt % of a non-hybrid-type cyclohexane 1,3-diester-based material represented by Formula 2; and
0.5 to 85 wt % of a non-hybrid-type cyclohexane 1,3-diester-based material represented by Formula 3.

8. The plasticizer composition of claim 1, which comprises:
based on the total weight of the plasticizer composition,
10 to 50 wt % of a hybrid-type cyclohexane 1,3-diester-based material represented by Formula 1;
0.5 to 50 wt % of a non-hybrid-type cyclohexane 1,3-diester-based material represented by Formula 2; and
35 to 80 wt % of a non-hybrid-type cyclohexane 1,3-diester-based material represented by Formula 3.

9. A method of preparing a plasticizer composition of claim 1, comprising:
providing more than one isophthalate-based material represented by Formula 4; and
preparing a cyclohexane 1,3-diester-based material mixture by hydrogenating the more than one isophthalate-based materials in the presence of a metal catalyst,

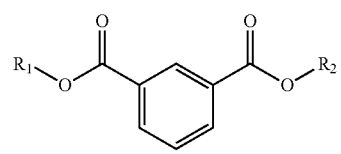
[Formula 4]

in Formula 4, $R_1$ and $R_2$ are different or the same, and each independently any one selected from the group consisting of a substituted or unsubstituted alkyl group having 3 to 10 carbon atoms, a substituted or unsubstituted alkylaryl group, a substituted or unsubstituted arylalkyl group, and a substituted or unsubstituted aryl group.

10. A resin composition, comprising:
100 parts by weight of a resin; and
5 to 150 parts by weight of the plasticizer composition of claim 1.

11. The resin composition of claim 10, wherein the resin comprises one or more selected from the group consisting of ethylene vinyl acetate, polyethylene, polypropylene, polyketone, polyvinyl chloride, polystyrene, polyurethane, a thermoplastic elastomer and a poly(lactic acid).

* * * * *